United States Patent [19]

Cavazza

[11] Patent Number: 5,863,940
[45] Date of Patent: Jan. 26, 1999

[54] MEDICAMENT AND THERAPEUTICAL METHOD FOR TREATING IDIOPATHIC ASTHENOZOOSPERMIA

[75] Inventor: Claudio Cavazza, Rome, Italy

[73] Assignee: Sigma-Tau HealthScience S.p.A., Pomezia, Italy

[21] Appl. No.: 980,821

[22] Filed: Dec. 1, 1997

[51] Int. Cl.$^6$ ........................ A61K 31/205; A61K 31/225
[52] U.S. Cl. ............................................ 514/547; 514/556
[58] Field of Search ..................................... 514/556, 547

[56] References Cited

PUBLICATIONS

R. Golan, et al., "Influence of various substrates on the acetylcarnitine:carnitine ratio in motile and immotile human spermatozoa", *Reprod. Fert.* (1986) 78, 287–293.

Sava R. Micic, et al., "Seminal Carnitine and Glucosidase in Oligospermic and Azoospermic Men", *Journal of Andrology*, vol. 15, Supplement 1994, p. 77S.

Koji Ashizawa, et al., "Inhibition of Flagellar Motility of Fowl Spermatozoa by L–Carnitine: Its Relationship with Respiration and Phosphorylation of Axonemal Proteins", *Molecular Reproduction and Development*, 38:318–325 (1994).

C. Jeulin, et al., "Uptake and release of free L–carnitine by boar epididymal spermatozoa in vitro and subsequent acetylation rate", *Journal of Reproduction and Fertility*, (1994), 100:263–271.

R. Deana, et al., "Effect of L–carnitine and L–Aminocarnitine on Calcium Transport, Motility, and Enzyme Release from Ejaculated Bovine Spermatozoa", *Biology of Reproduction*, 41:949–955 (1989).

A. Lee Carter, et al., "A factor in human seminal plasma which affects carnitine accumulation in bovine epididymal sperm", *Fertility and Sterility*, vol. 49, No. 5, May, 1988.

Claudette Jeulin, et al., "Acétylcarnitine et spermatozoïdes: relation avec la maturation épididymaire et la mobilitéchez le varrat et l'homme", *Reprod. Nutr. Dévelop.*, 1988, 28(5):1317–1328.

M. Bartellini., et al., "L–carnitine and acetylcarnitine in human sperm with normal and reduced motility", *Europaea Fertilitatis*, vol. 18, No. 1, 1987, pp. 29–31.

D.P. Shalev, "Investigation on the Motility of Human Spermatozoa in a Defined Medium in the Presence of Metabolic Inhibitors and of Carnitine", *Andrologia* 18(4):368–375 (1986).

G. Abbaticchio, et al., "Free L–carnitine in humn semen", *Archives of Andrology* 15:137–142 (1985).

G.F. Menhini–Fabris, et al., "Evaluation of Human Seminal Carnitine Content in the Pathophysiology of Reproduction", *3d International Forum of Andrology*, Paris, France, Jun. 18–19, 1985.

G. Fabrizio Menhini–Fabris, et al., "Free L–carnitine in human semen: its variability in different andrologic pathologies", *Fertility and Sterility*, vol. 42, No. 2, pp. 263–267, Aug., 1984.

David A. I. Suter, et al., "The concentrations of free L–carnitine and L–O–Acetylcarnitine in spermatozoa and seminal plasma of normal, fresh, and frozen human semen", *Fertility and Sterility*, vol. 31, No. 5, Mar., 1979, pp. 541–544.

S. Kohengkul, et al., "Levels of L–carnitine and L–O–Acetylcarnitine in normal and infertile human semen: a lower level of L–O–Acetylcarnitine in infertile semen", *Fertility and Sterility*, vol. 28, No. 12, Dec., 1977, pp. 1333–1336.

R. Amendola, et al., "Effects of L–acetylcarnitine (LAC) on the Post–Injury Recovery of Mouse Spermatogenesis monitored by Flow Cytomertyr 1. Recovery after X–Irradiation", *Andrologia* 21, (6):568–575 (1989).

G. Vitali, et al., "Carnitine Supplementation in Human Idiopathic Asthenospermia: Clinical Results", *Drugs Exptl. Clin. Res.* XXI(4) 157–159 (1995).

S. Micic, et al., "Does L–carnitine adminstered in vivo improve sperm motility?", *ARTA* 1995, vol. 7, pp. 127–130.

M. Costa, et al., "L–carnitine in idiopathic asthenozoospermia: a mulitcenter study", *Andrologia* 26, 155–159, 1994.

"Diagnostica Andrologica e Fisiopathologia della Riproduzione" 1995, Colle di Mezzo srl—Tutti i Diritti sono Riservati.

"Federation Proceedings—Abstract" 57$^{th}$ Annual Meeting, Atlantic City, New Jersey, Apr. 15–20, 1973: p. 528.

Amendola et al, Andrologia, 21(6), 568–75 (Abstract), 1989.

Vitali et al, Drugs. Exp. Clin. Res, 21(4) 157–9 (Abstract), 1995.

*Primary Examiner*—Leonard Schenkman
*Attorney, Agent, or Firm*—Oblon, Spivak, McClelland, Maier & Neustadt, P.C.

[57] ABSTRACT

A therapeutical method is disclosed for treating idiopathic asthenozoospermia which comprises orally or parenterally administering to a patient in need thereof a combination preparation comprising in admixture L-carnitine and acetyl L-carnitine or the pharmacologically acceptable salts thereof, in substantially equimolar amouts.

8 Claims, No Drawings

MEDICAMENT AND THERAPEUTICAL METHOD FOR TREATING IDIOPATHIC ASTHENOZOOSPERMIA

BACKGROUND OF THE INVENTION

1. Field of the invention

The present invention relates to a medicament and a therapeutical method for treating patients affected by idiopathic asthenozoospermia.

2. Description of the Pior Art

Idiopathic asthenozoospermia, a disorder of sperm motility, is a post-testicular cause of infertility due to various ethiology, i.e. congenital defects of the sperm tail, maturation defects, immunological disorders or infection.

Spermatozoa are produced in the testis and undergo post-gonadal modifications in the epididymis to acquire fertilizing ability. In epididymal plasma, high-molecular-weight proteins and such small molecules as free carnitine convert the gametes into "competent" and functional cells. Free L-carnitine is taken up from blood plasma and concentrated in the epididymal lumen. This epididymal secretion is beneficial for spermatozoa and is not merely an excretory waste. Free carnitine goes through the sperm plasma membrane by passive diffusion. Free L-carnitine is acetylated in mature spermatozoa only. The excess acetyl-CoA from the mitochondria is probably stored as acetyl-L-carnitine and modulates the reserves of free CoA essential to the function of the tricarboxylic acid cycle. This property of L-carnitine of buffering CoA in the mitochondrial matrix is known in somatic cells but is accentuated in male germinal cells. The relationship between the endogenous pool of free and acetylated L-carnitine and the percentage of progressive sperm motility indicates a more important metabolic function related to flagellar movement. Thus, the potential of initiating sperm motility which takes place in the epididymis is probably independent of the carnitine system while the energy properties of acetyl-L-carnitine is relevant in situations of "energy crisis". The uptake of cytoplasmic free L-carnitine in mature spermatozoa must be a protective form of mitochondrial metabolism useful to the survival of this isolated cell.

Several drugs for treating idiopathic asthenozoospermia, none of them completely satisfactory, are known.

Antiestrogen drugs (such as clomiphene citrate and tamoxifen) block sex hormones from inhibiting the Follicle Stimulating Hormone (FSH) and the Luteinizing Hormone (LH) in the brain. This triggers an increased release of LH and FSH, which in turn stimulates testosterone production. Increased testosterone level improves spermatogenesis, thus improving sperm density and motility. However a recent randomized, double-blind, multicenter study of 190 couples by the World Health Organization (WHO) showed no effect of clomiphene citrate. Tamoxifen was claimed to improve sperm concentration but no change in motility was usually detected. As for clomiphene, recent studies did not confirm its efficacy.

Testosterone Rebound therapy involves large doses of testosterone that suppress the activity of the patient's pituitary gland. This, in turn, reduces the intratesticular level of testosterone to systemic levels from the usual level. Then the androgen therapy is discontinued in the hope that the system will rebound and improved spermatogenesis will result.

This therapy is not recommended since a large number of treated patients continue to exhibit azoospermia after treatment.

Testolactone, an aromatase inhibitor, prevents the conversion of testosterone to estradiol. It has been tested in patients with idiopathic oligospermia but contrasting results have raised many doubts on its efficacy.

Mesterolone is a synthetic androgen widely used to treat idiopathic male infertility. A recent study sponsored by WHO failed to show any efficacy of this drug.

Human Chorionic Gonadotropin (HCG) is administered empirically to patients with defects in sperm count or motility to correct a presumed intratesticular deficiency of testosterone. Some patients actually experienced a depression of sperm count due to an increased estrogen production by the testes.

Human Menopausal Gonadotropin (HMG) has approximatively equal LH and FSH activity but its use has produced increased sperm counts in only about 50% of cases.

FSH and HCG or HCG and HMG combination therapy does not appear to improve these results any better.

Gonadotropin Releasing Hormone (GnRH) is expensive and disappointing results have been obtained.

Kallikrein can improve sperm motility with increases in sperm concentration but only in about 50% of cases.

Also L-carnitine and acetyl L-carnitine have been studied as candidate drugs for the treatment of asthenospermia.

Vitali G. et al. (Drugs Exptl. Clin. Res. XXI(4):157–159, 1995) investigated the effectiveness of L-carnitine administration in a group of patients with idiopathic asthenospermia. A favourable effect of the compound on sperm motility and rapid linear progression has been shown in 37 out of 47 patients treated. Same results were obtained by Török L. (Dermatol.Monatsschr. 169:572–575, 1983).

Costa M. et al. (Andrologia, 26:155–159, 1994) showed a significant improvement, both in a quantitative and qualitative manner, in spermatozoal motility after administration of L-carnitine. They speculated that in infertile patients impairment occured either in epididymal function or in the ability of sperm to capture and utilize carnitine (Bartelloni M. et al., Acta Eur. Fertil. 18:29–31, 1987). Thus, the administration of carnitine would provide additive substrate for sperm energy metabolism and motility.

Müller-Tyl E. et al. (Fertilität 4:1–4, 1988) suggested that L-carnitine therapy can be successful in infertile patients. In fact, results demonstrated a continuous increase in the carnitine levels in sperm following carnitine treatment and a contemporary increase in motility and sperm cell count.

Loumbakis P. et al. (XIIth Congress of the European Association of Urology. Paris, Sep. 1–4, 1996) provided preliminary data suggesting that carnitine administration may positively affect sperm quality.

Finally, Moncada M. L. et al. (Acta Eur. Fertil. 23(5):221–224, 1992) investigated the effect on sperm quality of acetyl-L-carnitine administered to patients affected by idiopathic oligoasthenospermia. Acetyl-L-carnitine had no effects on sperm density, but showed to increase progressive sperm motility.

SUMMARY OF THE INVENTION

It has now been found that the oral or parenteral administration of a combination preparation comprising in admixture L-carnitine and acetyl L-carnitine or the pharmacologically acceptable salts thereof in a molar ratio ranging from 1.5:1 to 1:1.5 is remarkably effective for treating idiopathic asthenozoospermia, even in those patients who were shown not to respond to treatment with the known, conventional aforesaid drugs.

It has also been found that the combination preparation of the present invention exhibit a marked superiority over the results obtained by administering L-carnitine or acetyl L-carnitine separately, i.e. as monotherapies.

DESCRIPTION OF SPECIFIC EMBODIMENTS

Preferably, the molar ratio between L-carnitine inner salt and acetyl L-carnitine inner salts or the pharmacologically acceptable salts thereof is 1:1.

The combination preparations of the present invention, when in unit dosage form, comprise from 0.33 g to 0.22 g of L-carnitine inner salt and from 0.28 g to 0.42 g of acetyl L-carnitine or equimolar amounts of the pharmacologically acceptable salts thereof.

Preferred combination preparations in unit dosage form comprise 0.22 g of L-carnitine inner salt and 0.28 g of acetyl L-carnitine inner salt or equimolar amounts of the pharmacologically acceptable salts thereof.

It was, furthermore, found that although the daily dose of the aforesaid active ingredients to be administered is determined from the age, weight and condition of the patient, utilizing sound professional judgement, it is generally advisable to administer in a single dose or multiple dose administration regimen 0.60–1.0 g/day of L-carnitine and 0.80–1.3 g /day of acetyl L-carnitine or equivalent molar amounts of the pharmacologically acceptable salts thereof. Larger doses can be safely administered in view of the extremely low toxicity of the aforesaid active ingredients.

A clinical study aimed at evaluating whether supplementation with the drug association therapy is effective in improving reduced sperm motility over L-carnitine monotherapy and acetyl L-carnitine monotherapy, respectively, is hereinbelow described.

Thirty-six patients responding to the following inclusion/exclusion criteria were enrolled. "Inclusion criteria: young, infertile males with idiopathic asthenozoospermia recognized as the sole cause of infertility at least two years duration; semen parameters to be met on at least two samples: sperm concentration (M/ml) between 10–20, motility (%)>20<40 at 2 hours, rapid linear progression (%)<20 at 2 hours.

Exclusion criteria: undescended testes, varicocele (grade 3), traumatic or infection related testicular atrophy, obstruction, inflammation and infection of the genital tract, any endocrine disorder affecting the hypothalamic-pituitary-gonadal axis; post-pubertal mumps, evidence of antisperm antibodies.

All patients gave their informed consent to this open study.

Semen was obtained by masturbation after at least four days of sexual abstinence. The samples were analysed within one hour after ejaculation for all the parameters by the standard methods recommended by the WHO (1987). The sperm motility was studied using a computer motility analyser on at least two specimens.

Semen analysis and motility assessment were carried out at baseline and after 4 months of L-carnitine (N=12) or acetyl-L-carnitine (N=12) or association drug (N=12) treatment.

L-carnitine was administered at the dose of 2 g/day (2×500 mg tablet b.i.d., after meals) for 4 months. Acetyl-L-carnitine was administered at the dose of 4 g/day (2×1 g sachet b.i.d., after meals) for 4 months. The association drug treatment (L-carnitine+acetyl-L-carnitine) was administered at the dose of 2 g/day (2×500 mg tablet composed of 220 mg L-carnitine and 280 mg acetyl-L-carnitine, b.i.d. after meals) for 4 months.

Data were analyzed using Student's "t" test for paired data.

Results

| | Semen analysis | | | | | |
|---|---|---|---|---|---|---|
| Variable (mean ± SD) | Baseline | L-Carnitine | Baseline | Acetyl-L-carnitine | Baseline | LC + ALC |
| Motility (%) | 26.8 ± 5.4 * | 33.1 ± 4.6 | 24.9 ± 4.5 # | 30.9 ± 4.5 | 26.3 ± 4.5 § | 40.8 ± 6.3 a b |
| Concentration (M/ml) | 15.7 ± 2.0 ** | 26.0 ± 2.8 b | 16.7 ± 3.6 | 18.1 ± 2.0 | 16.2 ± 2.4 § | 30.8 ± 3.6 a b |
| Spermatozoa with rapid linear progression (%) | 9.8 ± 1.5 ** | 17.0 ± 1.5 | 10.3 ± 1.1 b | 16.0 ± 1.2 | 10.0 ± 1.2 § | 21.6 ± 2.8 ** b |

LC + ALC = L-Carnitine + Acetyl-L-carnitine
* p ≤ 0.05 versus L-Carnitine
# p ≤ 0.05 versus Acetyl-L-carnitine
§ p ≤ 0.001 versus L-Carnitine + Acetyl-L-carnitine
a p ≤ 0.01 versus L-Carnitine
b p ≤ 0.001 versus Acetyl-L-carnitine
** p ≤ 0.001 versus L-Carnitine Before treatment values of seminal parameters were below those of WHO normal ranges.

The association drug treatment significantly increased the concentration and the motility of spermatozoa as well as the percentage of spermatozoa with rapid linear progression in comparison to L-carnitine and acetyl-L-carnitine monotherapy treatments.

The medicament of the present invention can be prepared by mixing the active ingredients (L-carnitine inner salt and acetyl L-carnitine inner salt or a pharmacologically acceptable salt thereof) with excipients suitable for the formulation of compositions which lend themselves to enteral administration (particularly oral administration) or to parenteral administration (particularly by the intramuscular or intravenous route). All such excipients shall be readily apparent to one having ordinary skill in this art.

Pharmaceutically acceptable salts of the aforesaid active ingredients include all pharmaceutically acceptable salts which are prepared by the addition of an acid to L-carnitine and acetyl L-carnitine inner salts and which do not give rise to undesired toxic or side effects. The formation of pharmaceutically acceptable acid addition salts is well known in pharmaceutical technology.

Non-limiting examples of suitable salts include chloride; bromide; iodide; aspartate, particularly acid aspartate; citrate, particularly acid citrate; tartrate; phosphate, particularly acid phosphate; fumarate, particularly acid fumarate; glycerophosphate; glucose phosphate; lactate; maleate, particularly acid maleate; orotate; oxalate, particularly acid oxalate; sulphate, particularly acid sulphate; trichloroacetate; trifluoro acetate and methanesulphonate.

What is claimed is:

1. An orally or parenterally administrable combination preparation for treating idiopathic asthenozoospermia comprising in admixture L-carnitine and acetyl L-carnitine or the pharmacologically acceptable salts thereof, in a molar ratio ranging from 1.5:1 to 1:1.5.

2. The preparation of claim 1, wherein said molar ratio is 1:1.

3. The preparation of claim 1 in unit dosage form comprising from 0.33 g to 0.22 g of L-carnitine and from 0.28 g to 0.42 g of acetyl L-carnitine or equimolar amounts of the pharmacologically acceptable salts thereof.

4. The preparation of claim 2 in unit dosage form comprising 0.22 g of L-carnitine and 0.28 g of acetyl L-carnitine or equimolar amounts of the pharmacologically acceptable salts thereof.

5. The preparation of claim 1 wherein the pharmacologically acceptable salt of L-carnitine and acetyl L-carnitine is selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, oxalate, acid oxalate, sulphate, acid sulphate, trichloroacetate, trifluoro acetate, and methanesulphonate and mixtures thereof.

6. A therapeutical method for treating idiopathic asthenozoospermia which comprises orally or parenterally administering to a patient in need thereof a combination preparation comprising in admixture L-carnitine and acetyl L-carnitine or the pharmacologically acceptable salts thereof, in a molar ratio ranging from 1.5:1 to 1:1.5.

7. The method of claim 6, wherein said molar ratio is 1:1.

8. The method of claim 6 which comprises orally or parenterally administering to said patients in a single or multiple dose administration regimen a total amount of 0.60–1.0 g/day of L-carnitine and 0.80–1.3 g/day of acetyl L-carnitine or equimolar amounts of the pharmacologically acceptable salts thereof.

* * * * *